US006332891B1

(12) United States Patent
Himes

(10) Patent No.: US 6,332,891 B1
(45) Date of Patent: Dec. 25, 2001

(54) SYSTEM AND METHOD FOR PERFORMING IMAGE GUIDED SURGERY

(75) Inventor: David M. Himes, Los Gatos, CA (US)

(73) Assignee: Stryker Corporation, Kalamazoo, MI (US)

(*) Notice: Subject to any disclaimer, the term of this patent is extended or adjusted under 35 U.S.C. 154(b) by 0 days.

(21) Appl. No.: 09/251,138

(22) Filed: Feb. 16, 1999

(51) Int. Cl.[7] ................................................. J61B 17/32
(52) U.S. Cl. ............................................. 606/169; 606/130
(58) Field of Search .................................... 606/130, 164, 606/167, 170; 600/914, 411, 417; 604/116; 128/897

(56) References Cited

U.S. PATENT DOCUMENTS

| 5,669,921 | * | 9/1997 | Berman et al. ........................ 606/167 |
| 5,676,673 | | 10/1997 | Ferre et al. . |
| 5,803,089 | * | 9/1998 | Ferre et al. ........................... 128/897 |
| 5,810,809 | * | 9/1998 | Rydell .................................... 606/49 |
| 5,829,444 | | 11/1998 | Ferre et al. . |
| 6,090,123 | * | 7/2000 | Culp et al. ............................ 606/180 |

OTHER PUBLICATIONS

PCT Application No. PCT/US97/15242 (WO 98/06338), published Feb. 19, 1998, 183 pages.
InstaTrak® System, *Operator's Manual*, 1997, pp. 1–48 and 63–105.
AESCULAP ELAN®-E Electronic Surgical Motor System, Jan., 1999.

* cited by examiner

Primary Examiner—Allan N. Shoap
Assistant Examiner—Lien Ngo
(74) Attorney, Agent, or Firm—Flynn, Thiel, Boutell & Tanis, P.C.

(57) ABSTRACT

A power tool system (24) for use with an image guidance system (28) to perform image guided surgery. The power tool system includes a handpiece (48) to which a powered cutting accessories (26) are selectively attached. A coupling assembly (50) releasbly holds a cutting accessory to the handpiece. A state marker (204) is connected to the coupling assembly. The state marker undergoes a state transition whenever the coupling assembly undergoes a run state/accessory load state transition. A sensing unit (34) integral with the image guidance system is releasbly attached to the handpiece. The sensing unit includes a sensing element (238) that provides an output signals indicative of the position of the sensing unit and handpiece. The sensing unit also includes a handpiece state sensor (240) that provides an indication of the state of the state marker. Once the image guidance system is calibrated for a cutting accessory, the system presents an image of the position of the cutting accessory. If the coupling assembly is moved to the accessory load state to facilitate the attachment of a new cutting accessory, the change in state of the output signal from the handpiece state sensor prompts the image guidance system to require the user to calibrate the system for the new cutting accessory. If the cutting accessory is a motor driven tool, the tool system includes a drive unit (42) separate from the handpiece with an electric motor (44). Rotational power developed by the motor is transferred to the handpiece by a flexible drive shaft (46).

19 Claims, 12 Drawing Sheets

SYSTEM AND METHOD FOR PERFORMING IMAGE GUIDED SURGERY

FIELD OF THE INVENTION

This invention relates generally to a system and method for performing image guided surgery. More particularly, this invention relates to a system and method for performing image guided surgery with a powered surgical handpiece to which different cutting accessories may be attached.

BACKGROUND OF THE INVENTION

Medical imaging techniques, such as computerized axial tomography (CAT) and magnetic resonance image (MRI), now allow medical personal to view three-dimensional images of the organs and tissue within a person. This equipment is used both to diagnose a patient's condition and as an aid in performing surgical procedures. Specifically, it is now possible, to a limited extent, for doctors to perform what is referred to as image guided surgery.

In image guided surgery, an image is initially generated of the body region in which the surgical procedure will be performed. A small transmitter is then placed on the patient. This transmitter is held in place by an appropriate harness or strap to ensure that its position stays constant relative to fixed tissue internal to the patient. Owing to the physical structure of the harness/strap, the position of the transmitter to the fixed tissue points internal to the patient are also known.

Then, the surgical procedure is performed using an instrument to which a complementary sensor is attached. This sensor is a receiver that, based on signals generated by the transmitter, generates output signals representative of its position relative to the transmitter. During surgery, these output signals are forwarded to a processing unit which also maintains data representative of the previously obtained image of the patient's body region. Thus, the processing unit contains data representative of the image of the patient's body, the distance between the transmitter and the patient's fixed tissue points and the distance between the transmitter and the sensor. Using these data, the processor is able to generate data that inferentially identifies where, inside the patient, the instrument is located. This data is then superimposed as a distinct image on an output display on which an image of the patient's body is presented. Thus, the surgeon performing the procedure is able to see where, in the body, the instrument is located even though the surgical site is not directly exposed to the eye.

The development of image guided surgery is making it possible for surgeons to more accurately and easily perform procedures in which the surgical site is concealed or difficult to view. For example, being able to perform image guided surgery is especially useful when performing sinus surgery in which the surgical instruments are inserted into the patient through an existing body opening. Also, being able to precisely identify the location of the surgical instrument can be helpful when performing endoscopic surgery. In this type of surgery, small portals are cut in the patient and elongated instruments are inserted into the portals and positioned at concealed surgical sites. Also, being able to precisely locate surgical tools is important when performing spinal or neurological surgical procedures.

To date, however, the ability to perform image guided surgery is limited. This is because only a few surgical instruments have been designed to work with a key complementary component, the sensor, that makes image guided surgery possible. For example, there have been some probes and aspirators designed to be attached to the sensor. However, it has been very difficult to provide powered surgical tools that can be used to perform image guided surgery. There are several reasons for this. One reason for this is that many powered surgical tools include a handpiece in which there is an electrically driven motor. The magnetic fields that develop when the motor is actuated can interfere with the readings taken by the position-defining sensor.

Moreover, most powered surgical tools are designed to drive a number of different complementary cutting accessories. Common accessories these tools drive include edgers, resectors, shavers, planers and burrs. An advantage of designing a powered surgical tool so that it can be used with these different accessories is that it allows the surgeon, during an operation, to simply change the accessory in order to accomplish a specific surgical procedure. Moreover, by making cutting accessories removable, these accessories can be made disposable. This eliminates the otherwise high costs associated with manufacturing the cutting accessories out of repetitively sterilizable material and the actual expenses associated with sterilizing them. A problem when using these cutting accessories for image guided surgery is that each accessory has unique dimensions. When a cutting accessory is attached to the handpiece, the overall data regarding the dimensions of the surgical tool change. The processor associated with the image generator must take into account this change in the dimensions of the surgical tool in order to ensure that the processor generates data that accurately indicates where, in the patient's body, the tool is located.

To date, it has been difficult to provide a powered surgical tool system that can be used in conjunction with image generating system without affecting the image generating systems sensor and that is configured to ensure that, when the tool's accessory is changed, the image-generating system will continue to properly indicate the location of the tool.

SUMMARY OF THE INVENTION

This invention is directed to a new and improved surgical tool system designed to be used with an image generating system in order to facilitate the performance of image guided surgery. The surgical tool system of this invention includes a handpiece that powers a cutting accessory and that is formed out of material that is either non-magnetic or that has very low magnetic permeability. The handpiece is further provided with members designed to allow an image generating system sensing unit to be coupled to the handpiece. Owing to the nature of the material from which the handpiece is formed, its actuation does not effect the signal processing of the complementary sensing unit.

The handpiece of this invention is provided with a coupling assembly designed to facilitate the removable attachment of different cutting accessories to the handpiece. Integral with the coupling assembly is state marker. When the coupling assembly is moved from a run position to a position in which a new accessory can be loaded, the state marker undergoes its own state transition. In one version of the invention, the state marker is physically displaced. The displacement of the state marker is monitored by a complementary handpiece state sensor integral with the image generating system sensing unit. If the handpiece state sensor detects a change in the position of the state marker, the sensor, in turn, transmits a signal representative of this transition to the processor integral with the image generating system. The processor, upon receipt of the signal that the coupling system has been actuated, prompts the surgeon to recalibrate the handpiece for the new cutting attachment. This ensures that the image generating system produces images that accurately identify the location of the cutting attachment relative to the portion of the patient's body in which it is inserted.

BRIEF DESCRIPTION OF THE DRAWINGS

The invention is pointed out with particularity in the claims. The above and further advantages of the invention may be better understood by reference to the following description taken in conjunction with the accompanying drawings, in which:

DETAILED DESCRIPTION

Figure 1:
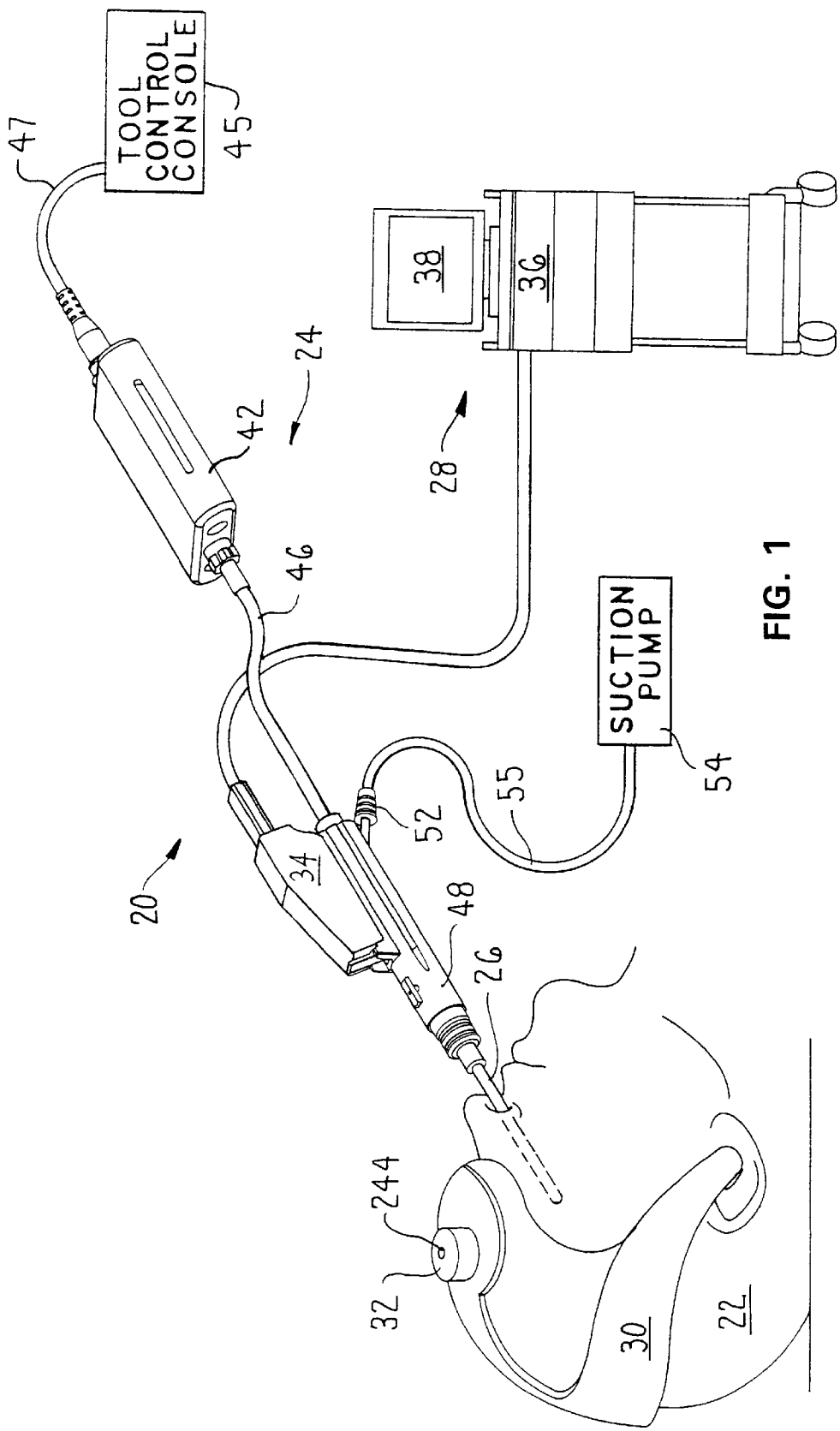
FIG. 1 depicts how the system and method of this invention is employed to perform image-guided surgery.

FIG. 1 depicts a powered surgical tool system 20 of this invention and how the system is employed to perform an image guided surgical procedure on a patient 22. The tool system 20 includes a powered surgical tool 24. A cutting accessory 26, such as a shaver blade, is attached to the distal end of the surgical tool 24 and is used to perform a surgical procedure on a patient. (Hereinafter "distal" shall be understood to mean towards the surgical site within the patient 22; "proximal" shall be understood to mean away from the surgical site.) Here, the cutting accessory 26 is placed through the nostril of the patient 22 in order to perform a procedure on the patient's sinus system.

An image generating system 28 provides a image that indicates where, inside the patient's sinus system, the distal end of the cutting accessory 26 is located. The image generating system 28 includes a headset 30 that is fitted to the patient 22. A small transmitter 32 is attached to headset 30. Transmitter 32 broadcasts electromagnetic waves in a distinct, well defined pattern. A sensing unit 34 is attached to a portion of the tool 24 to which the cutting accessory 26 is attached. The sensing unit 34 is an electromagnetic wave receiver that is capable of generating output signals that indicate the position of the sensing unit 34 relative to the transmitter 32. The signals generated by sensing unit 34 are forwarded to a processor 36 also part of the image generating system 28.

Prior to performing a surgical procedure, a medical imaging device, such as CAT scanner or MRI scanner, is used to generate an image of the patient's body at the surgical site. This scanning process is also used to determine the position of the headset 30 relative to fixed tissue internal to the patient 22 at or near the body site at which the surgical procedure is to be performed. When the surgical procedure is performed, the position of the transmitter 32 relative to the headset 30 is known. Therefore, the position of the transmitter 32 relative to the patient's fixed tissue is inferentially determined. Prior to the beginning a surgical procedure with any cutting accessory 26, the tool 24 and sensing unit 34 are calibrated in order to provide a measure of the distance from the sensing unit 34 to the distal end of the cutting accessory 26.

During the surgical procedure, sensing unit 34 generates output signals that indicate its location relative to the transmitter 32. Accordingly, the image generating system processor 36 has within it data representative of: the image of the patient's body; the location of the transmitter 32 relative to the patient's fixed body tissue; the location of the sensing unit 34 relative to the transmitter 32; and the location of the distal end of the cutting accessory 26 relative to the sensing unit 34. Using these data, the processor 36 inferentially determines the position of the distal end of the cutting accessory 26 relative to the patient's fixed tissue. Once processor 36 makes this determination, the processor generates an image on a display 38 that indicates where, inside the patient's body, the distal end of the cutting accessory 26 is located. The surgeon uses this image as a guide for manipulating the cutting accessory 26 and performing the surgical procedure. A more detailed description of how the image generating system 28 is able to provide images that depict the location of the cutting accessory 26 inside the patient 22 is found in U.S. Pat. No. 5,676,673, entitled POSITION TRACKING AND IMAGING SYSTEM WITH ERROR DETECTION FOR USE IN MEDICAL APPLICATIONS, issued on Oct. 14, 1997 which is incorporated herein by reference.

Figure 2:
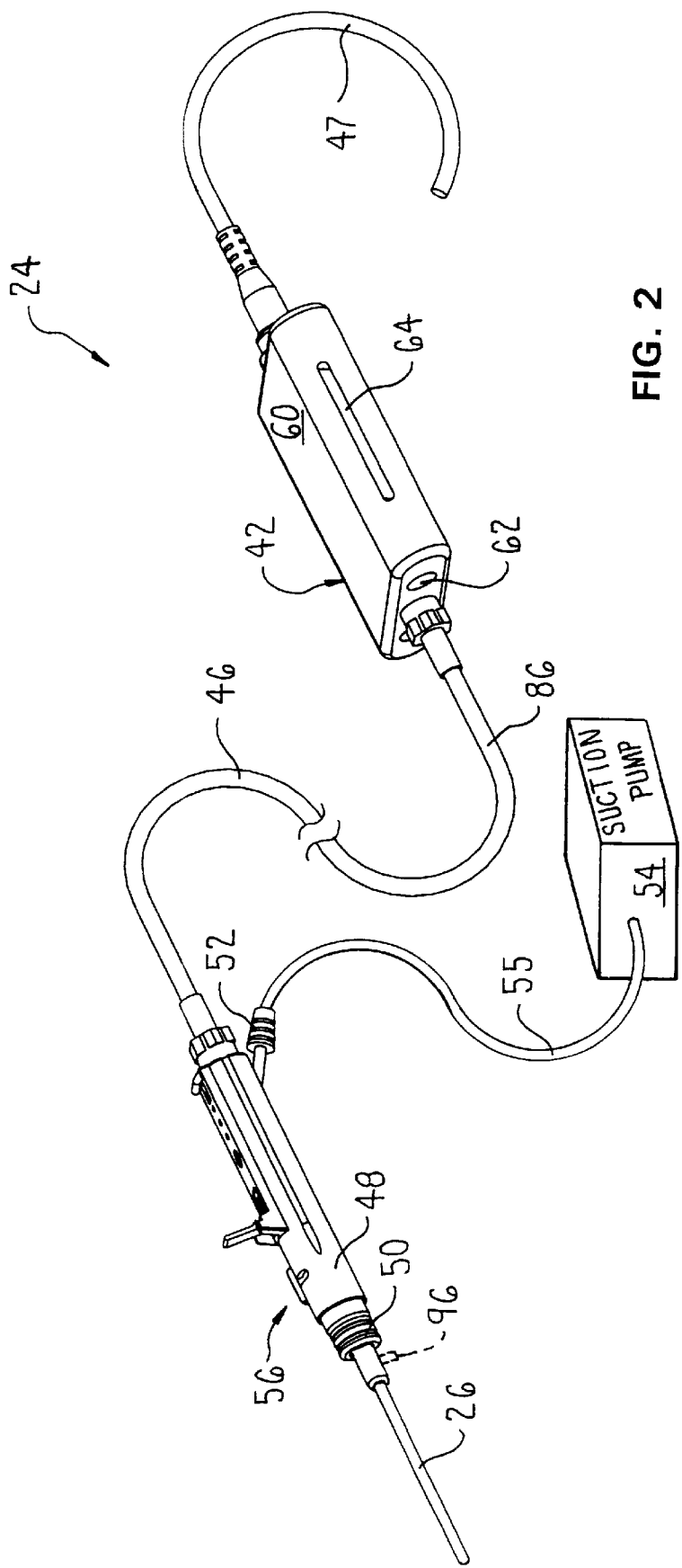
FIG. 2 depicts the powered surgical tool employed to perform surgery according to this invention.

The powered surgical tool 24 of the system 20 of this invention is now generally described with respect to FIGS. 1 and 2. The tool 20 includes a drive unit 42 in which an electric motor 44 (FIG. 3) is housed. Motor 44 is supplied with a drive current from a control console 45 over a power cord 47. One such control console 45 that can be used to supply power to drive unit 42 is the TPS™ control console manufactured by the inventor's Assignee. The rotational power developed by motor 44 is applied to a flexible drive shaft 46 attached to the front of the drive unit 42.

The distal end of the flexible drive shaft 46 is attached to a handpiece 48. The handpiece 48 is the component of the tool 24 that is actually held and manipulated by the surgeon. A coupling assembly 50 attached to the distal end of the handpiece 48 rotatably and releasably holds the cutting accessory 26 to the handpiece. It will be observed from FIG. 1 that the handpiece 48 is the component of the tool 24 to which sensing unit 34 is releasably attached.

The handpiece 48 of the depicted version of tool 24 further includes a suction fitting 52 through which a suction is drawn through the cutting accessory 26 and the handpiece. The suction is drawn in order to remove irrigating fluid and debris from the surgical site. The suction is drawn by a suction pump 54 connected to fitting 52 by a suction tube 55. The suction pump 54 is a standard surgical suction pump not part of this invention not described any further. The handpiece 48 is provided with a suction valve 56 that allows the surgeon to control the suction applied to the surgical site.

Figure 3:
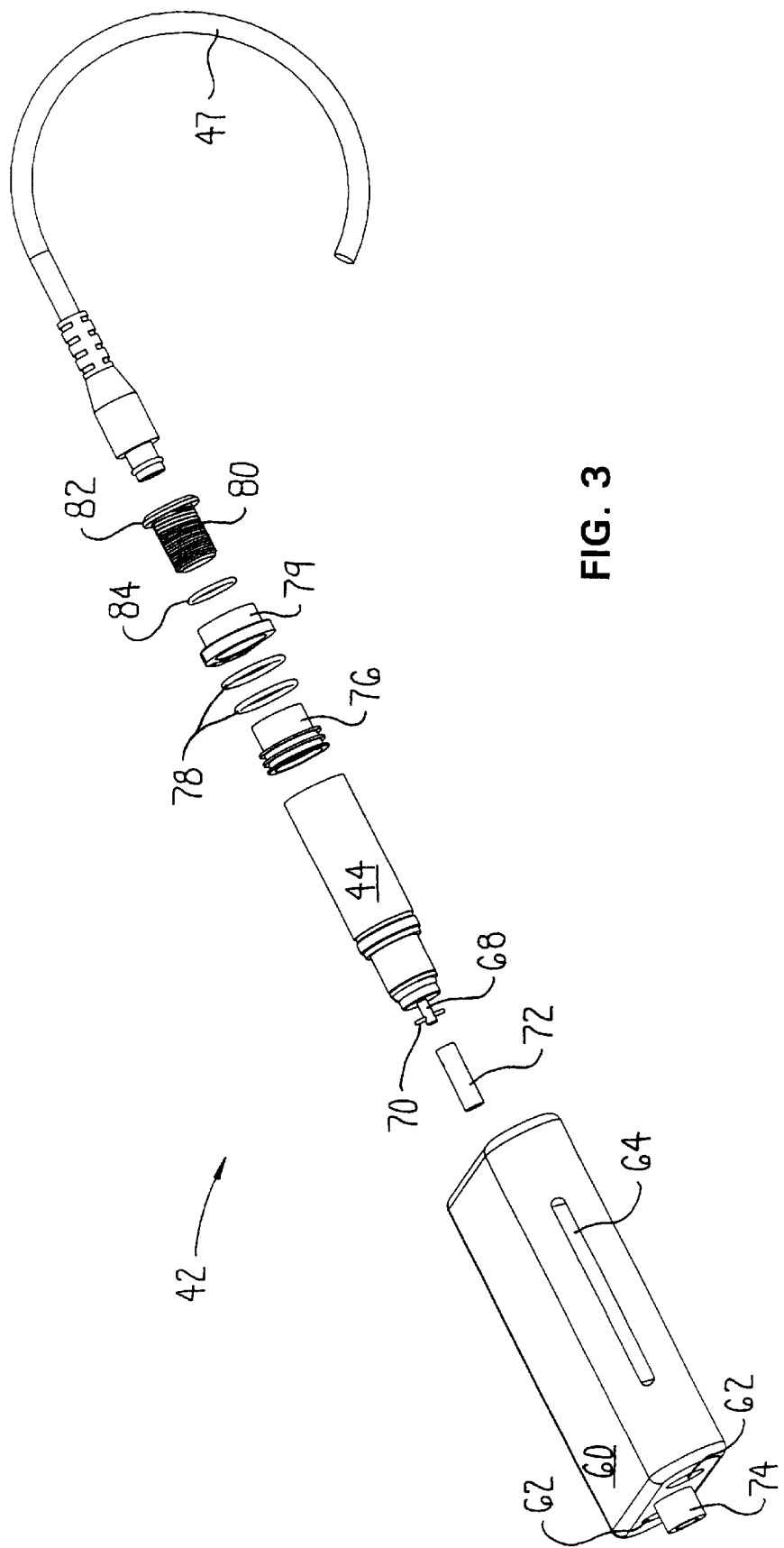
FIG. 3 is an exploded view of the drive unit of the powered surgical tool.
Figure 4:
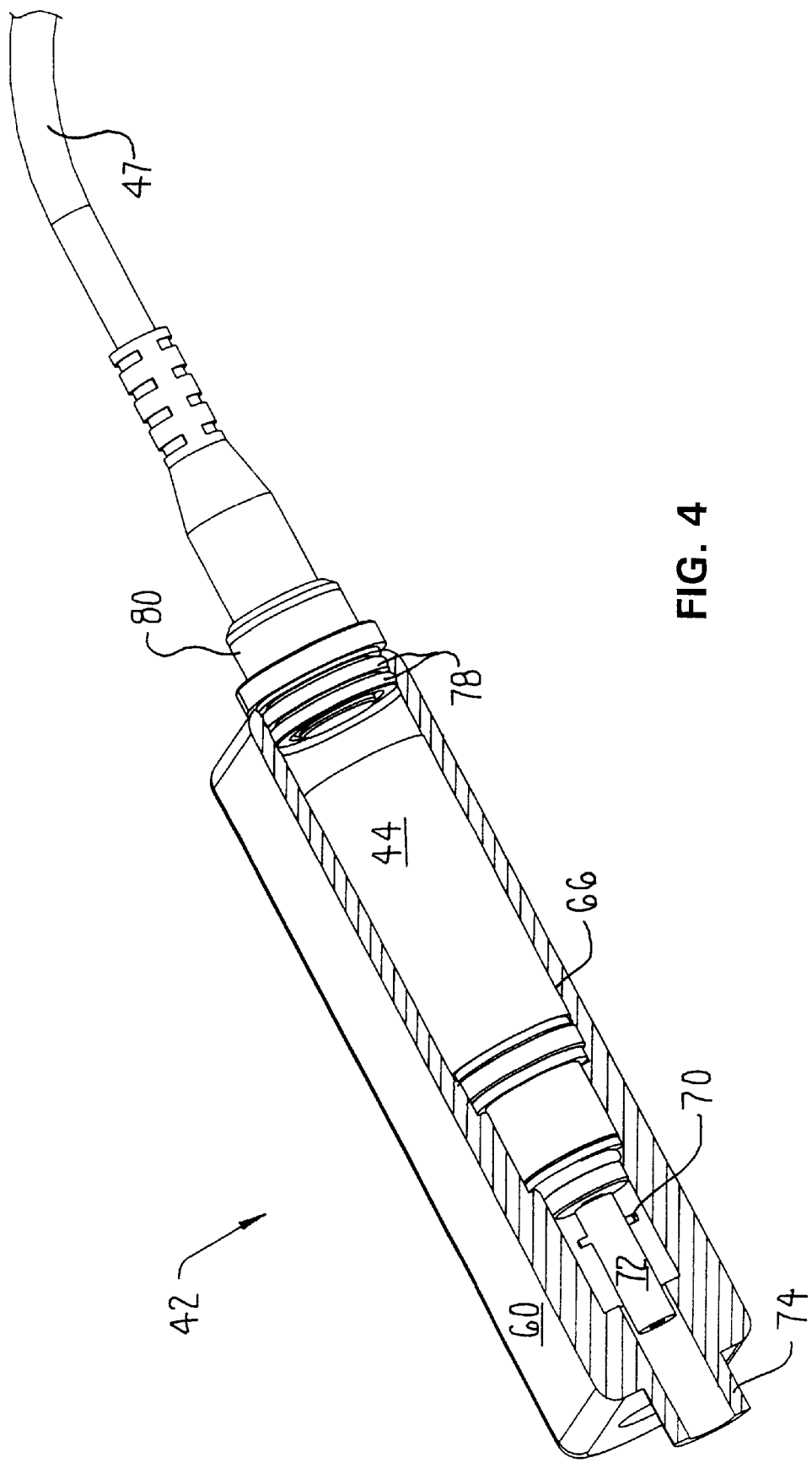
FIG. 4 is a cross-sectional view of the drive unit.

With this basic understanding of the structure of the surgical tool 24, the construction of the drive unit 42 is now explained in detail by reference to FIGS. 3 and 4. Drive unit 42 includes a metal base 60 that serves as a housing for the other components of the drive unit. It will be observed that base 60 has a bottom that is approximately 10 cm in width and is formed from 303 stainless steel (SST). Base 60 is provided with a wide profile so that it is a stable object. The stability of the base 60 prevents the drive unit 42 from vibrating when the motor 44 is actuated. The base 60 is further formed so that the outer sections thereof, the sections on the opposed sides of motor 44, have defined through bores 62. The presence of through bores 62 reduce the overall weight of the base 60. The base 60 is also formed with two slots 64 (one shown). Each slot 64 extends diagonally from a side wall of the base 60 through to the bottom surface of the base. The slots 64 facilitate the attachment of a strap to the base which is used to ensure the base cannot be inadvertently bumped or tipped during a surgical procedure.

Base 60 is further formed so as to define a main bore 66 that extends longitudinally through the base along the center axis of the base between bores 62. Main bore 66 serves as the space within base 60 in which the actual drive components of drive unit 42 are housed. Specifically motor 44 is seated within main bore 66. The motor 44 is any suitable motor for driving cutting accessories 26. In many preferred versions of the invention, motor 44 is a DC motor. In more preferred versions of the invention, motor 44 is a brushless, sensorless DC motor. The motor 44 includes a rotor 68 that extends out of the distal end of the cylindrical housing, (not identified) that contains a gear reduction assembly coupled to the motor. A pin 70, formed from 303 SST, is mounted to the exposed end of rotor 68. Pin 70 extends perpendicularly relative to the axis of rotor 68.

A sleeve-like drive tube 72 is fitted over the exposed end of rotor 68. Drive tube 72 is provided with slots, (not identified) to facilitate seating the drive tube over the exposed ends of pin 70. As a consequence of the drive tube's 72 engagement of pin 70, the drive tube rotates in unison with rotor 68. The drive tube 72 serves as a coupling between the motor rotor 68 and a complementary coupling member integral with the proximal end of the flexible drive shaft 46. It will further be observed that the distal end of the drive unit base 60 is formed with a forward-extending neck 74. Neck 74, which is open ended, surrounds main bore 66 and provides mechanical protection to the end of the flexible drive shaft 46 seated in base 60.

A cylindrical seal retainer 76 is seated in the proximal end of main bore 66 behind motor 44. Two O-rings 78 are mounted to the outside of seal retainer 76 to provide a seal between the retainer and the adjacent interior wall of base 60 that defines main bore 66. A connector housing 79 is permanently attached to the proximal end of the base that defines the main bore 66. An electrical connector 80 is threadedly secured inside connector housing 79. Electrical connector 80 serves as the mechanical interface between the conductors extending from motor 44, (conductors not illustrated) and the plug integral with the distal end of power cord 47. The electrical connector 80 has an exposed head 82 that has a diameter greater than that of the threaded body of the connector. An O-ring 84 is compressed between the undersurface of electrical connector head 82 and connector housing 78 to provide a seal between the electrical connector and the housing.

The flexible drive shaft 46 has an outer shell 86 formed from a flexible, sterilizable plastic. A flexible drive cable, (not illustrated,) is located inside shell 86. The drive cable can, for example, be formed out of a helically wrapped cable that rotates along its center axis but is otherwise flexible. One suitable cable is available from Suhner Manufacturing, Inc. of Rome, Georgia.

Figure 5:
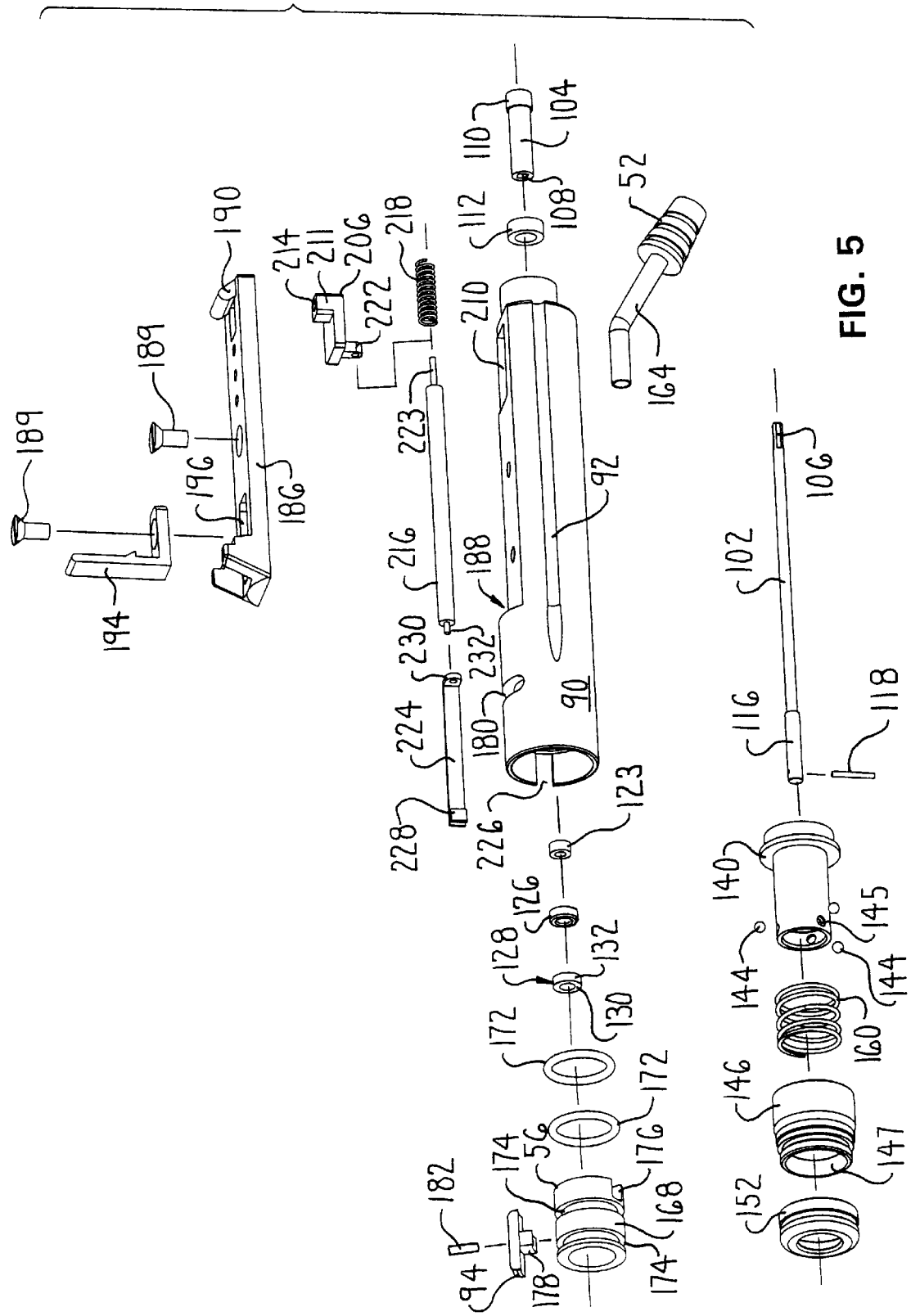
FIG. 5 is an exploded view of the handpiece of the powered surgical tool.
Figure 6:
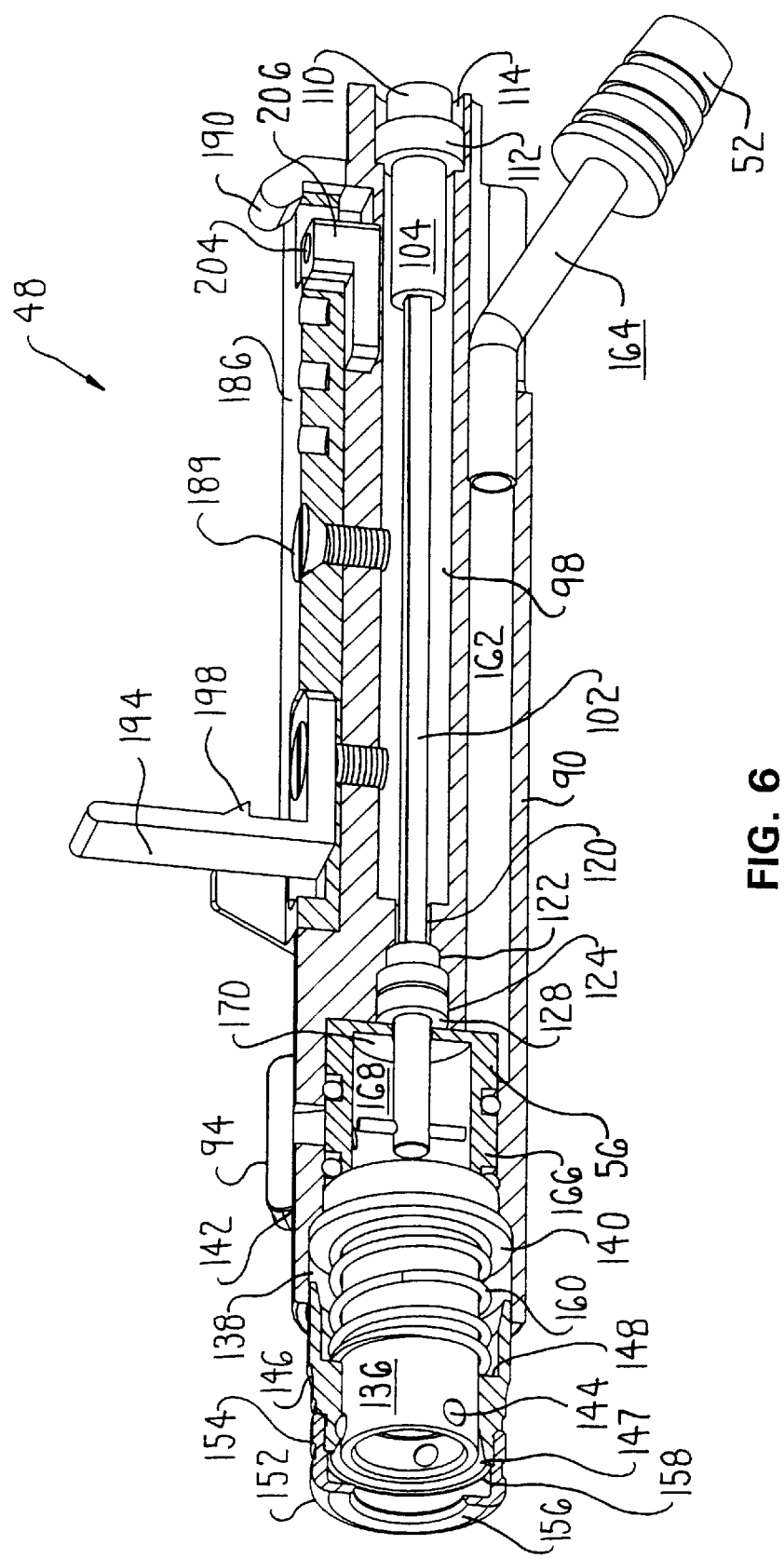
FIG. 6 is a cross-sectional view of the handpiece illustrating the drive shaft.

The handpiece 48 of the surgical tool 24 of this invention is now described by initial reference to FIGS. 5 and 6. The handpiece 48 has a base 90 of generally cylindrical shape and is formed from a rigid, sterilizable plastic such as polyether ether ketone (PEEK). The outer surface of base 90 is formed to have a groove 92 that extends longitudinally from the proximal end of the handpiece 48 to a immediately behind a finger switch 94 integral with the suction valve 56. Groove 92 is provided to allow an irrigation fluid supply line, (not illustrated and not part of this invention,) to be releasably fitted to handpiece 48. The irrigation fluid supply line provides irrigating fluid to an inlet port 96 integral with the cutting accessory 26 (FIG. 1) so that the irrigating fluid can be discharged from the distal end of the cutting accessory. The coupling assembly 50 is fitted to the distal end of base 90. Suction valve 56 is located inside base 90 behind the coupling assembly 50. The flexible drive shaft 46 is attached to the proximal end of base 90.

The handpiece base 90 is formed with a shaft bore 98 that expends axially through the base from the proximal end to a position behind suction valve 56. An elongated drive shaft 102 is rotatably mounted in shaft bore 98. Drive shaft 102 is a solid cylindrical tube that is formed of a sterilizable metal that has a very low magnetic permeability. One particular metal from which drive shaft 102 may be formed is 303 SST. A coupler 104 formed from 303 SST is fitted over the proximal end of drive shaft 102. To facilitate the mating of the coupler 104 to the drive shaft 102, the proximal end of the drive shaft is formed to have planar facets 106. This shaping of the drive shaft allows the end of the drive shaft to be fitted into a complementary shaped opening 108 in the adjacent end of the coupler 104. This arrangement ensures that the drive shaft 102 and coupler 104 rotate in unison.

The coupler 104 has an exposed head 110. Head 110 is formed with an opening 111 (FIG. 7) designed to receive a complementary connector integral with flexible drive shaft 46. Thus, coupler 104 transfers the rotational power provided from flexible drive shaft 46 to the drive shaft 102 integral with handpiece 48. A bearing assembly 112 is fitted around coupler 104 immediately behind head 110. The bearing assembly 112 provides a low friction interface between coupler 104 and the adjacent interior wall of handpiece base 90. More particularly, in the illustrated version of the invention, base 90 is formed with an enlarged diameter counterbore 114 that is coaxial with and forms the proximal end for shaft bore 98. Bearing assembly 112 is located in counterbore 114 and is seated against the annular step located between shaft bore 98 and counterbore 114.

The distal end of drive shaft 102, the end adjacent coupling assembly 50, is formed to have a cylindrical head 116 that has a diameter greater than that of the body of the drive shaft. The head 116 of the drive shaft 102 is seated inside the suction valve 56 as will be discussed in more detail hereinafter. A pin 118, formed from 303 SST, extends perpendicularly through head 116. A hub integral with the cutting accessory 26, (hub not shown) seats over the head 116 and the exposed ends of pin 118. The hub engages pin 118 to cause the cutting accessory 26 to rotate in unison with the drive shaft 102.

The portion of the drive shaft 102 that extends from shaft bore 98 to head 116 extends through distinct coaxial bores formed in the handpiece 90. Immediately forward of shaft bore 98, base 90 is formed to have a neck bore 120. Neck bore 120 has a diameter significantly less than that of shaft bore 98. Forward of neck bore 120, the base is formed with bearing bore 122. Bearing bore 122 has a diameter greater than that of the adjacent neck bore 120. A bearing assembly 123 is fitted around the section of the drive shaft 102 that extends through bearing bore 122. Bearing assembly 123 provides a low friction interface between the distal end of the drive shaft 102 and the adjacent interior wall of base 90. Bearing assembly 123 is formed from the same material from which bearing assembly 112 is formed. The base 90 is further formed with a seal bore 124 that is located between bearing bore 122 and suction valve 56. Seal bore 124 is slightly larger in diameter than bearing bore 120. A quad seal 126 formed from a rubber compound sold under the trademark Viton by Parker Seal of Pleasantville, Calif. is seated in seal bore 124 around the portion of the drive shaft 102 that extends through the seal bore. Quad seal 126 thus provides a liquid tight seal between the drive shaft 102 and the adjacent inner wall of handpiece base 90 that defines seal bore 124.

An insert 128, formed of aluminum, is fitted over the quad seal 126 to hold the quad seal in place. The insert 128 has a disc-like base 130 with a center opening through which the drive shaft 102 extends. Integrally formed with base 130 is an annular lip 132 that extends around the perimeter of the base rearwardly towards the proximal end of the handpiece 48. Lip 132 is thus seated between the annular side surface of quad seal 126 and the adjacent inner wall of the base. Since insert 128 is compression fit in seal bore 124, the insert holds the quad seal 126 in the a bore 124.

The coupling assembly 50 has a tube-like front cap 136 that extends forward from the distal end of the handpiece base 90. In the depicted version of the invention, it can be seen that the base 90 is formed with a coupling bore 138 that extends rearward from the distal end of the base towards the drive shaft 102. The front cap 136 is formed from 303 SST.

While front cap 136 is generally cylindrical, the cap is formed to have a ring-like flange 140 that extends perpendicularly outwardly relative to the longitudinal axis of the cap. Flange 140 is seated inside coupling bore 138. More particularly, the undersurface of flange 140, the surface directed towards the proximal end of the handpiece 48, is seated against an inwardly directed circular step 142 formed by base 90. Step 142 divides coupling bore 138 into two sections, a first, relatively small diameter section, adjacent suction valve 56 and a second, relatively large diameter section that extends from the step to the open end of the bore 138. Complementary threading along the inside wall of the base 90 defining the coupling bore first-section and the adjacent outer surface of the front cap 136 releasably secure the front cap to the base (threading not illustrated).

Three metal ball bearings 144 are seated in separate holes 145 formed in the distal end of front cap 136 that extends forward of base 90. The holes 145 have a cross sectional profile equal to that of a section slice through a sphere. More particularly, front cap 136 is formed so that the diameter of the openings into the holes 145 from the inside wall of the front cap is less than the diameter of ball bearings 144. Thus, the shape of the holes 145 prevent the bearings from passing therethrough into the center or the front cap 136.

A cone sleeve 146 is fitted around the exposed end of front cap 136 so as to surround bearings 144. The cone sleeve 146 is formed so that the inner wall thereof has a frusto-conical section 147 that tapers inwardly from the distal end of the sleeve. The cone sleeve 146 is further formed so as to have an outwardly directed step 148 located rearward of holes that extends away from front cap 136. The body of the cone sleeve 146 which extends rearward from the outer perimeter of step 148 projects into the open end of coupling bore 138.

A nose cap 152 is threadedly secured to the distal end of the cone sleeve 146. More specifically, nose cap 152 has a sleeve-like base 154. The inner wall of base 154 is provided with threading that interlocks with complementary threading formed along the outer wall of cone sleeve 146, (threading not identified). The nose cap 152 is further formed to have a lip 156 that extends inwardly towards the center axis of the handpiece 48 from the distal end of base 154. The nose cap 152 is further dimensioned so that lip 156 is positioned to be located forward of the front end of the cone sleeve 146. The forward-extending portion of the nose cap base 154 and lip 156 collectively define an annular space 158 the purpose of which will be explained below. Both the cone sleeve 146 and nose cap 152 are formed from 303 SST.

Coupling assembly 50 further includes a compression spring 160 that surrounds the outer surface of front cap 136. The compression spring 160, which is made of stainless steel, extends between the outer surface of front cap flange 140 and cone sleeve step 148. Compression spring 160 urges the cone sleeve 146 and nose cap 152 in the forward direction, towards the distal end of cutting accessory 26. The spring-induced displacement of the cone sleeve 146 forces the reduced diameter portion of the frusto-conical section 147 towards holes 145. Thus, the frusto-conical section 147 of the cone sleeve 146 is forced against the bearings 144 to urge the bearings inwardly. This displacement of the bearings 144 holds the bearings in a complementary annular groove defined by a static hub integral with the cutting accessory 26 (hub not illustrated). Thus, compression spring 160, cone sleeve 146 and bearings 144 cooperate to hold the cutting accessory 26 to the handpiece 48. When the cutting accessory 26 is so coupled to the handpiece 48, the coupling assembly 50 is referred to as being in the run state.

The cutting accessory 26 is released from the handpiece 48 by an individual pushing the cone sleeve 146 and nose cap 154 downwardly, towards the proximal end of the handpiece. This action results in a like translation of annular space 158 so that the annular space 158 surrounds the outer surface of the front cap 136 adjacent holes 145. Once this space is so realigned, when the individual pulls outwardly on the cutting accessory 26, the bearings 144 are free to move into the space 158. Thus, the bearings 144 do not offer any resistance to the removal or replacement of the cutting accessory 26. When the coupling assembly 50 is in this state, it is referred to as being in the accessory load state. The coupling assembly 50 is returned to the run state by simply releasing the manual force used to force the cone sleeve 146 and nose cap 154 towards the base 90. Spring 160 urges the cone sleeve forward back to its static, run, position.

The suction fitting 52, which is formed from 303 SST, extends rearwardly from the proximal end of the handpiece base 90 and is in fluid communication with a suction bore 162 that extends axially through the base. In the depicted version of the invention, suction fitting 52 has an angled stem 164 that extends away from base 90. Thus, the actual fitting of the suction fitting 52 is spaced away from coupler 104. This separation facilitates the connection of suction tube 55 to the fitting 52.

The suction bore 162 is located below and is parallel with shaft bore 98. The suction bore 162 extends from a location forward of the proximal end of the handpiece base 90 to a valve space 166 formed in the base. The valve space 166, which has a circular profile and is dimensioned to receive suction valve 56, is located between seal bore 124 and coupling bore 138. More particularly, from the perspective view of the handpiece of FIG. 7, it can be seen that the valve space 166 is contiguous with the first, small diameter section of coupling bore 138. In the depicted handpiece 90, valve space 166 has a diameter greater than that of seal bore 124. Also in the depicted handpiece 90, suction bore 162 opens into the proximal end and lower portion of the side of the valve space 166 as seen in FIGS. 6 and 7.

The suction valve 56, which is of generally cylindrical shape, is closely fitted for rotation in valve space 166. The suction valve 56 has a tube-like main body 168 which is open towards the adjacent front cap 136 of coupling assembly 50. The suction valve 56 is further provided with an end plate 170 located at the proximal end of the main body 168. End plate 170 is seated in the base of valve space 166, the portion of the valve space located adjacent seal bore 124. Two O-rings 172 are located around the outside of the main body 168 to provide a seal between the outer wall of the main body and the adjacent inner wall of the base 90 that defines valve space 166. Each O-ring 172 is seated in a separate annular groove 174 located around the outer surface of main body 168.

Figure 7:
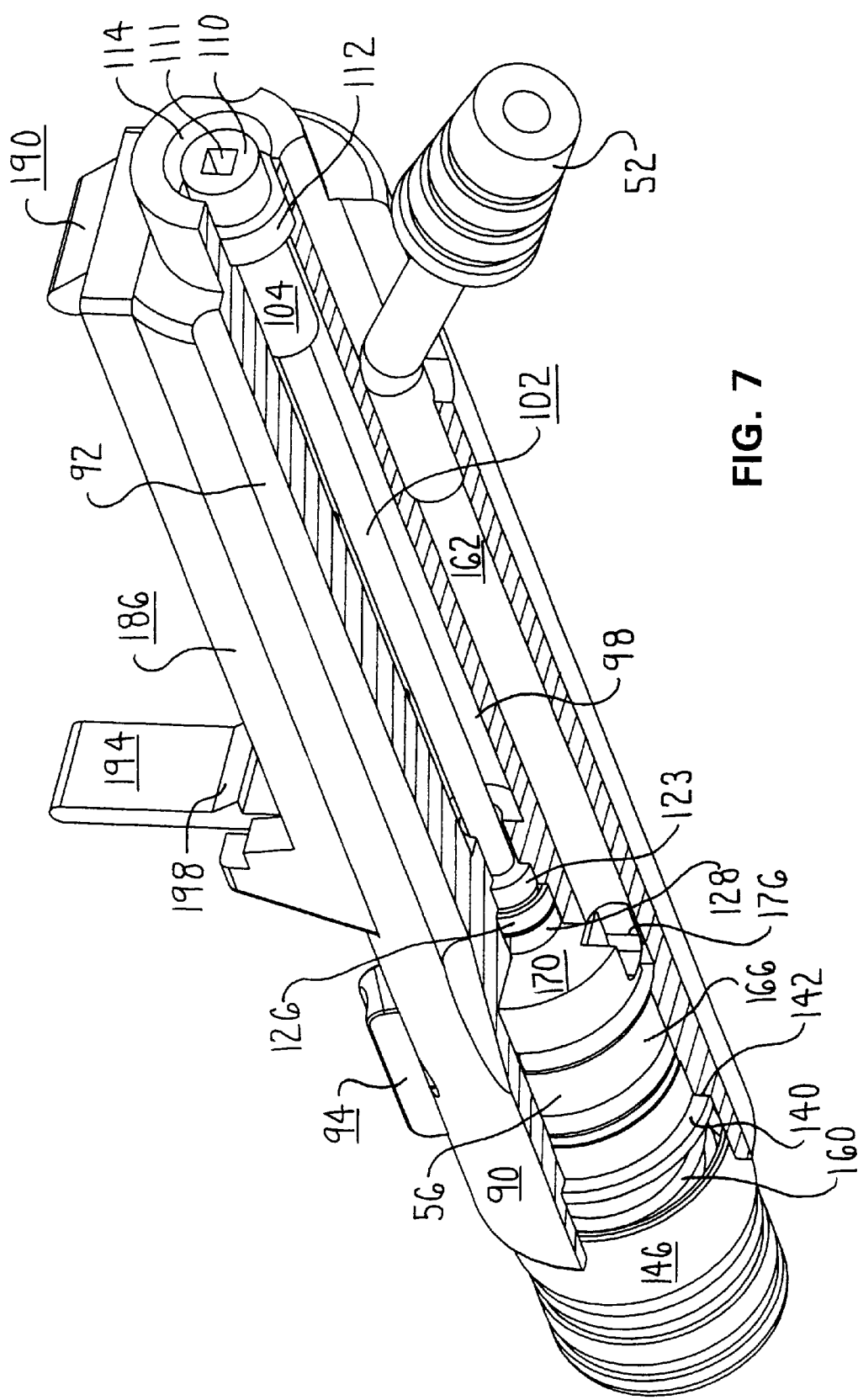
FIG. 7 is a cutaway view of the handpiece depicting how the suction valve regulates fluid flow through the suction bore.

Suction valve 56 is further formed to have a small through-opening 176 which is located in a proximal portion of main body 168 and the adjacent portion of the end plate 170, as seen best in FIG. 7. The suction valve 56 is placed in the open-state by rotating the valve so that through-opening 176 is positioned to allow fluid flow from the space in the center of the main body 168 to the suction bore 162. Suction valve 56 is closed by rotating the valve so that through opening 176 is out of registration with the suction bore 162. When the valve 56 is so positioned, the valve main body 168 blocks fluid from entering the suction bore 162.

The rotational position of the suction valve 56, the open/closed state of the valve, is controlled by finger switch 94. The finger switch 94 has a base 178 that extends through a radial slot 180 formed in the handpiece base 90 to the valve main body 168. A set screw 182 holds the finger switch 94 to the valve main body 168. The suction valve 56 and finger switch 94 are formed from 303 SST.

Handpiece 48 includes a receiver 186 to which the image-generating system sensing unit 34 is releasably mounted. The receiver 186, which has a generally elongated shape, is seated in a cut-out space 188 defined by the top of handpiece base 90. The receiver 186 and space 188 both extend forward from the proximal end of the base 90 to a position rearward of finger switch 94. The receiver 186 is formed out of PEEK. Screws 189 formed out of 303 SST secure the receiver 186 to the handpiece base 90. The proximal end of the receiver 186 is shaped to have a mounting finger 190 that extends diagonally upward to the distal end of the handpiece 48. Finger 190 seats in a complementary notch 192 (FIG. 9) in the sensing unit 34 to facilitate the securement of the sensing unit to the handpiece 48.

A latch 194 is mounted to the distal, front end of the receiver 186 to contribute to the removable securement of the sensing unit 34 to the handpiece 48. The latch 194, which is generally L-shaped, is formed out of a flexible, sterilizable plastic such as a acetal resin plastic sold under the trademark DELRIN by the DuPont Company of Delaware. The horizontal portion of latch 194 seats in a complementary recess 196 formed in the front end of the receiver 186. The forward one of the screws 189 that holds the receiver 186 in position holds extends through the horizontal portion of latch 194 to hold the latch in place. The vertical portion of the latch 194 is formed with a triangularly shaped tongue 198 that is directed towards the proximal end of the handpiece 48. Tongue 198 seats in a notch 202 in the front of the sensing unit 34 to hold the sensing unit in place. The sensing unit 34 is released from the handpiece 48 by pulling forward on latch 194 so that tongue 198 disengages from notch 202.

The handpiece 48 of the system 20 of this invention also includes a state marker that provides an indication to the sensing unit 34 when the coupling assembly 50 is displaced from the run state to the accessory load state. In the depicted version of this invention, the state marker is a magnet 204 that is displaced upon the actuation of the coupling assembly 50. The magnet 204 is held in a trolley 206 that is mounted for movement in the handpiece 48.

Figure 8:
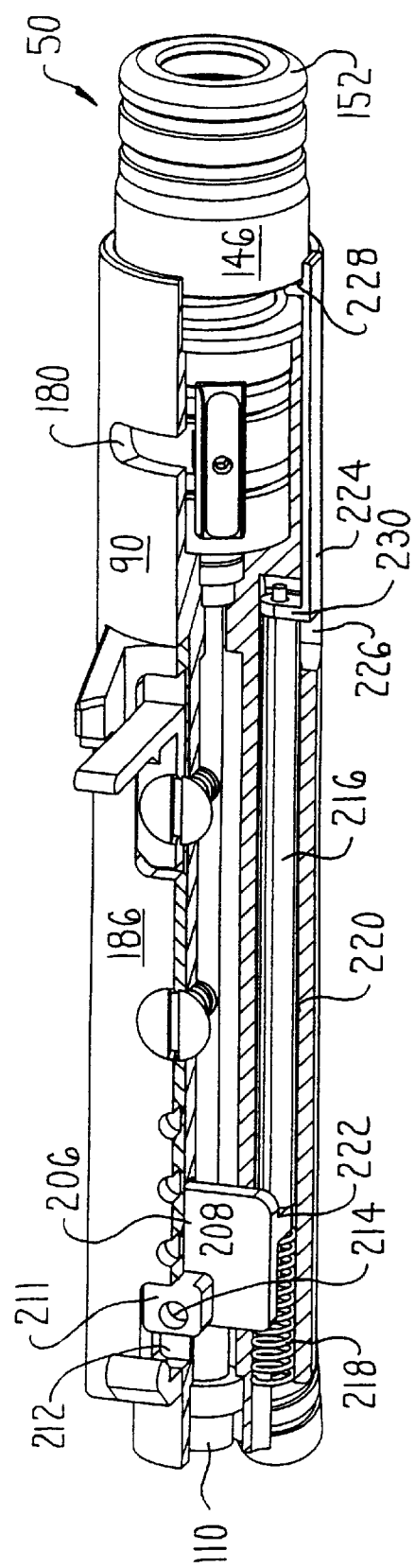
FIG. 8 is a cutaway view of the handpiece depicting how a magnet, which functions as a state marker, is coupled to the cutting attachment coupling assembly.

The trolley 206, now described by reference to FIGS. 5 and 8, is formed of PEEK plastic and has a main body 208. The main body of the trolley is seated in a recess 210 formed in the top of the handpiece base 90. Recess 210 has a length longer than that of the main body 208. This allows the trolley 206 to have a limited degree of movement along a path-of-travel parallel to the longitudinal axis of the base 90. The receiver 186 covers the forward portion of the recess 210, the portion located towards the distal end of the handpiece 48. A rectangular protrusion 211 extends up from the top surface of main body 208. The protrusion 211 is located adjacent the rear edge of the main body along one side of the main body 208. The protrusion 211 is located in a through hole 212 formed in the receiver 186. Through hole 212 is dimensioned so that when trolley 206 is displaced, the protrusion 211 can travel back and forth in the through hole. The protrusion 211 is formed with an opening 214 in which the magnet 204 is seated.

Movement of the trolley 206 is controlled by a reach rod 216 and a trolley spring 218. Both the reach rod 216 and the trolley spring 218 are disposed in an elongated rod shaft 220 formed in the handpiece base 90 which extends from a point located rearward of finger switch 94 to the proximal end of the body. The trolley 206 has a small tab 222 that extends downwardly from main body 208 into the rod shaft 220. In the depicted version of the invention, tab 222 is located on the side of main body 208 opposite the side from which protrusion 211 upwardly extends.

Reach rod 216, which is formed from PEEK plastic, has a rearwardly extending pin 223 that extends through a hole, (not identified) in trolley tab 222. Trolley spring 218, which is formed from stainless steel, extends from the proximal end of rod shaft 220 around the end of pin 223 so as to abut the rearwardly facing surface of the trolley tab 222. The plug integral with the distal end of flexible drive shaft 46 covers the open proximal end of rod shaft 220. The plug thus serves as the surface against which the trolley spring 218 abuts. Thus, trolley spring 218 biases the trolley tab 222 so that the trolley 206 is normally urged in the forward direction. The forward movement of the trolley 206 is blocked by the abutment of the main body 208 of the trolley against the interior wall of the base 90 that defines the front end of recess 210.

A plunger 224, in cooperation with the reach rod 216, displaces the trolley rearward whenever the coupling assembly 50 is moved from the run state to the accessory load state. The plunger 224 is flat piece of 303 SST which extends from the cone sleeve 146 to the reach rod 216. The plunger 224 is seated in a slot 226 formed in the outer surface of the handpiece base 90. Slot 226 extends rearwardly from the distal end of the base 90 to a point where the slot just overlaps and is in communication with the rod shaft 220.

The plunger 224 is shaped to have L-shaped, forward extending bracket 228 that is parallel with the distal end of the plunger. The plunger 224 is positioned so that the proximal end of the cone sleeve 146 is seated in the interstitial space between the distal end of the plunger and bracket 228. The proximal end of the plunger 224 is shaped to have a foot 230 that extends perpendicularly relative to the longitudinal axis of the plunger. The foot 230 extends into the rod shaft 220. The distal end of reach rod 216 is formed with a pin 232 that seats in a hole, (not identified) in the plunger foot 230. Trolley spring 218, in addition to normally urging trolley 206 forward, also urges reach rod 216 in the same direction. Thus, the reach rod 216 likewise urges the plunger 224 forward so that the plunger seats against cone sleeve 146.

Figure 9:
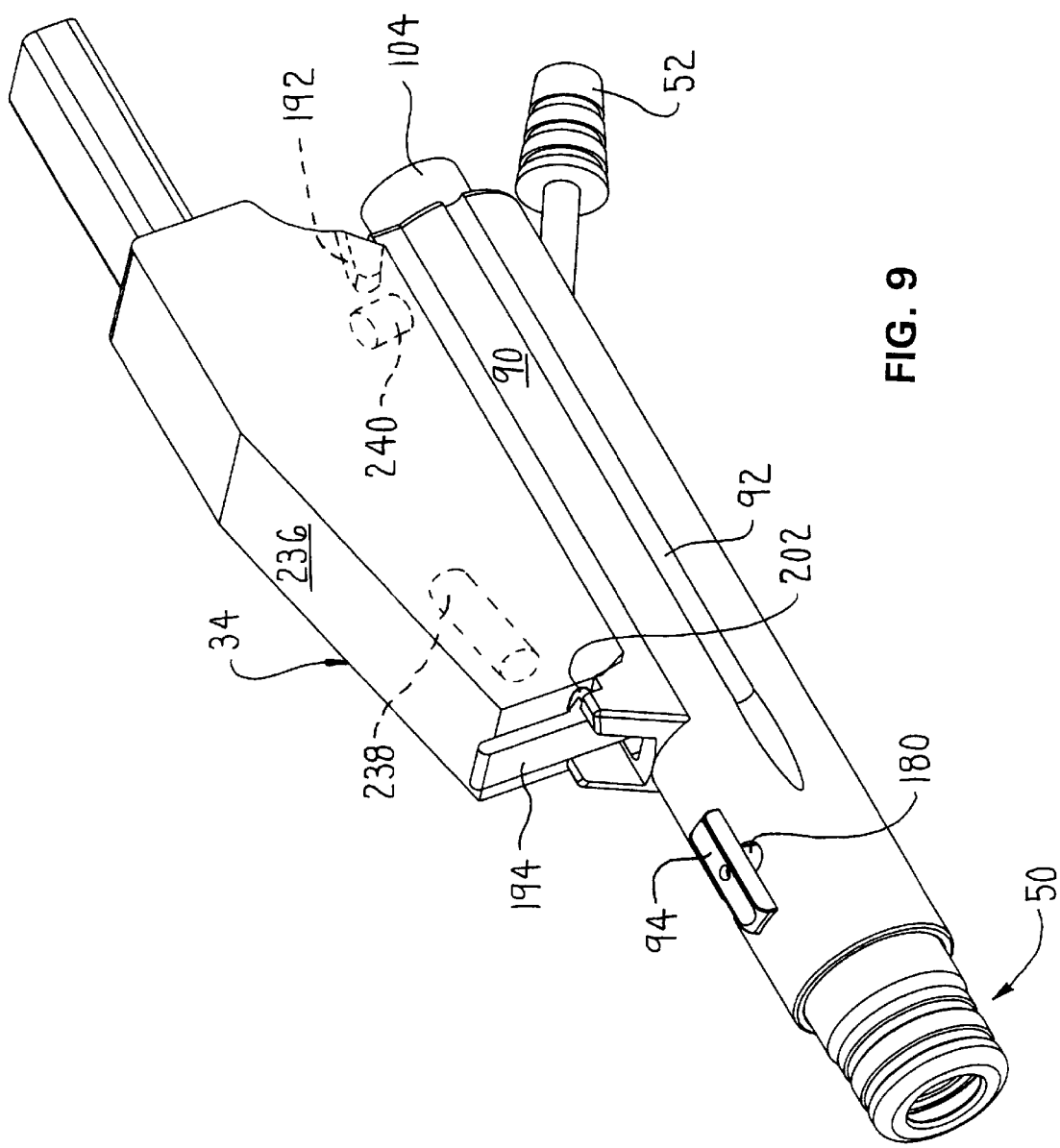
FIG. 9 is a perspective view of the image generating sensing unit sensing unit showing the sensing unit fitted to the handpiece.

As seen best by FIG. 9, the sensing unit 34 of the image generating system 28 includes a housing 236. The housing 236 is formed to define notches 192 and 202 in which, respectively, finger 190 and latch 194 of the handpiece 48 seat. At least one sensing element 238 (depicted as a phantom block) is seated inside the housing 236. In the depicted version of the invention, the sensing element 238 is located in the forward part of the housing 236, the part located closest to the distal end of handpiece 48. The sensing element 238 is the component of the sensing unit 34 that receives the signals broadcast by the transmitter 32 and converts those signals into sensed position signals. The sensed position signals are the signals the sensing unit 34 forwards to the processor 36.

The sensing unit 34 is further provided with a handpiece state sensor 240 (depicted in phantom). The handpiece state sensor 240 is located inside housing 236 so as to be adjacent magnet 204 when trolley 206 is in its normal, forwardly located position. Handpiece state sensor 240 is any suitable sensor, such as a Hall effect sensor, for monitoring the strength of an adjacent magnetic field. The handpiece state sensor 240 produces an output signal, a handpiece state signal, which varies as a function of the location of magnet 204 relative to the sensor.

Figure 10:
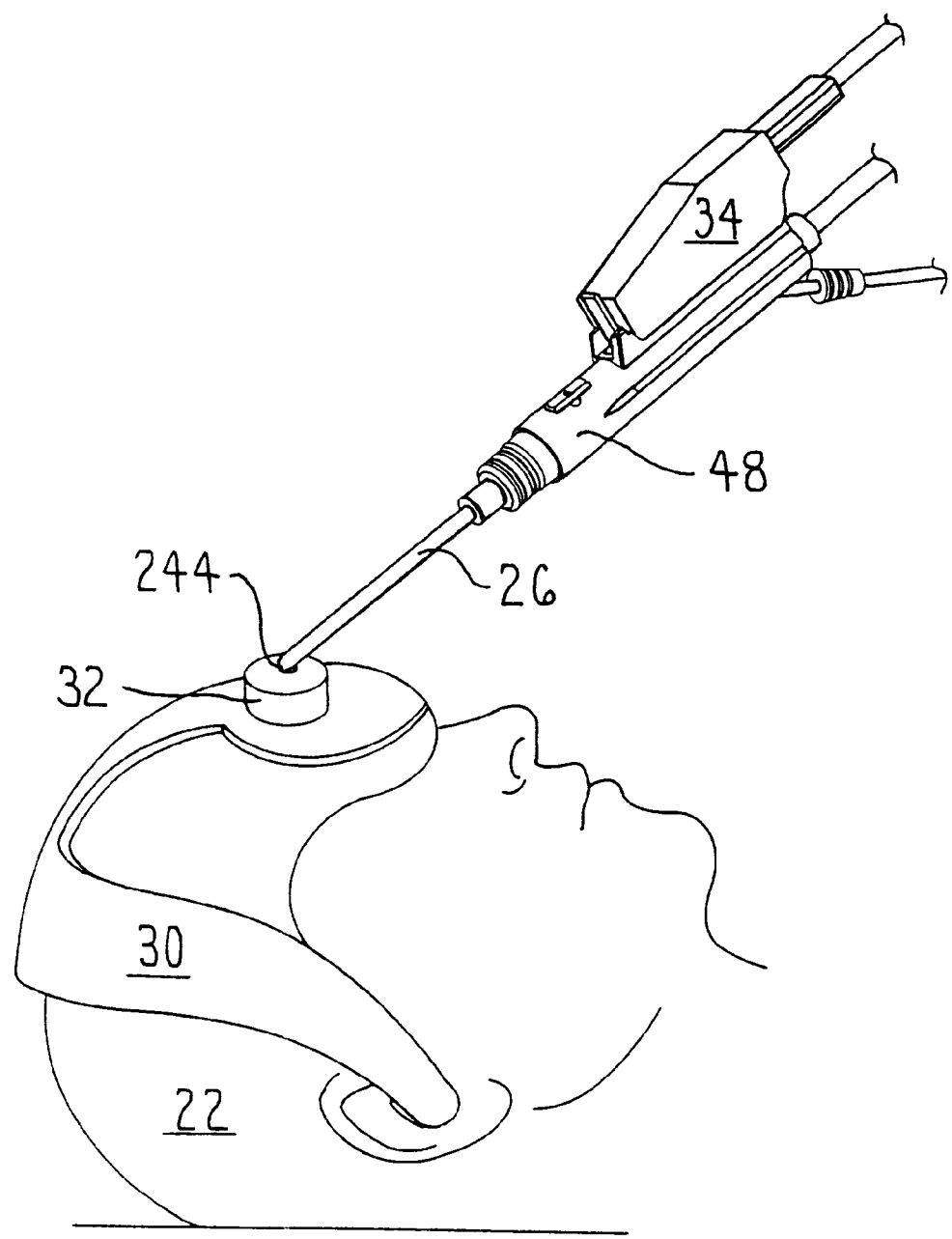
FIG. 10 depicts how the surgical tool system of this invention is calibrated.

The calibration of the surgical tool system 20 of this invention is now explained by reference to FIG. 10. The transmitter 32 of the image generating system 28 is constructed so that the outer case thereof has a dimple 244 on the outer surface thereof. After a cutting accessory 26 is attached to the handpiece 48, the distal tip of the cutting accessory is momentarily seated in the dimple 244. The image generating system 28 is then actuated so that the sensing element 238 internal to the sensing unit 34 generates signals that indicate the distance from the sensing element to the transmitter 32. At the time this distance measurement is made, the location of the distal end of the cutting accessory 26 is known. Therefore, using the data indicative of the transmitter-to-sensing element distance, the processor 36, by inference, calculates the position of the distal end of the cutting accessory 26 relative to the sensing element 34.

Once this calibration process is performed, the surgeon can perform image guided surgery using the handpiece 48 and cutting accessory 26. Throughout the surgical procedure, the sensing element 238 continually generates sensed position signals that indicate its position relative to the transmitter 32. Thus, the processor 36 is provided with data representative of: the position of the transmitter 32 relative to the patient's fixed tissue; the position of the sensing element 238 relative to the transmitter; and the position of the distal end of the cutting accessory 26 relative to the sensing element. Using these data, processor 36 calculates the position of the distal end of the sensing element relative to the patient's fixed tissue. Once this calculation is performed, the processor generates an image that indicates the position of the distal end of the cutting accessory 26 relative to the patient's fixed tissue. This image, which is presented on display 38, is used as guide by the surgeon for manipulating the handpiece-cutting accessory and performing the surgical procedure.

Figure 11:
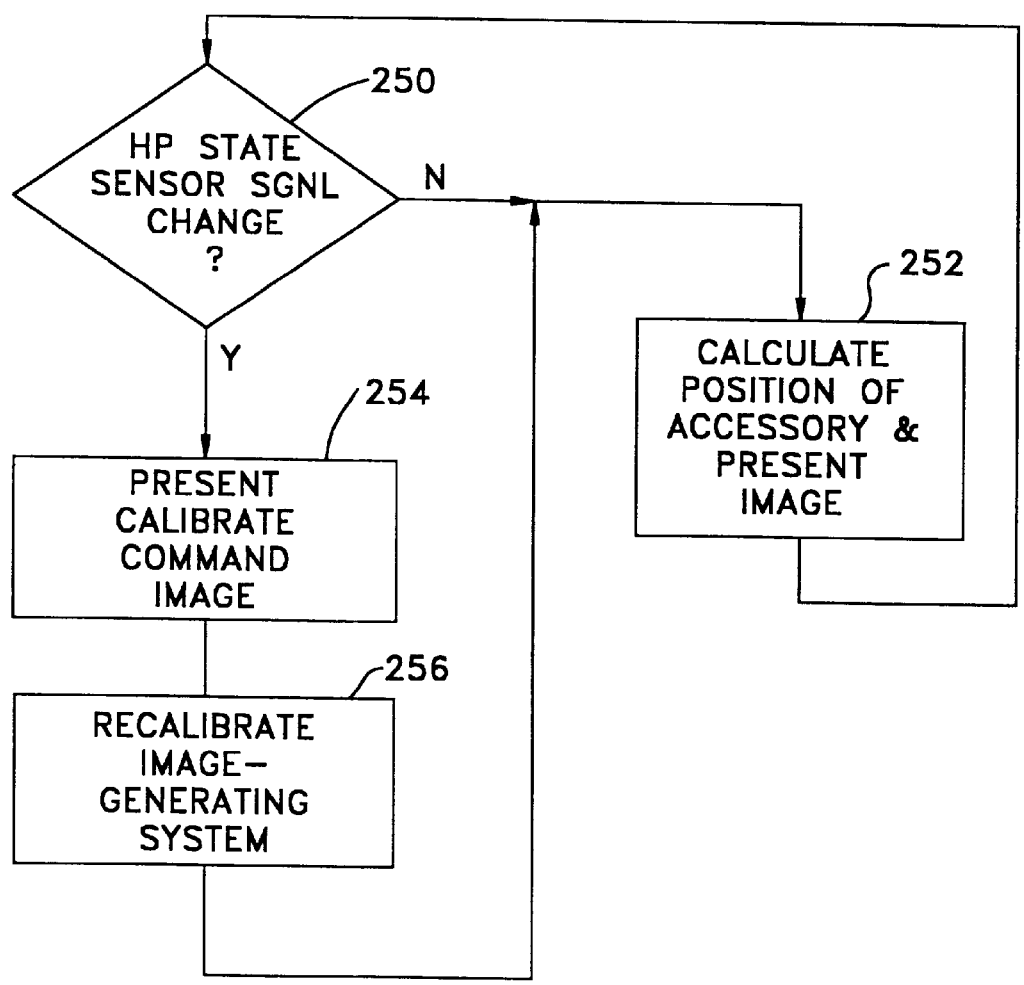
FIG. 11 is a flow chart depicting the process steps that are executed when a surgeon changes the cutting accessory used with the power tool of this system.

The system 20 of this invention is further provided with a failsafe to prevent the generation of images that, after the cutting accessory 26 has been changed, incorrectly indicate the position of the cutting accessory. As represented by step 250 of FIG. 11, processor 36 continually monitors the state of the output signal from the handpiece state sensor 240. This signal stays constant as long as the coupling assembly 50 is not shifted from the run state to the accessory load state. As long as this signal stays constant, the processor 36 continues to execute the processing steps required to calculate the position of the cutting accessory 26 and to generate an image representative of that position, step 252. Either concurrently or sequentially with the execution of step 252, processor 36 continually performs step 250 to determine if the output signal from handpiece state sensor output signal.

During a surgical procedure, a surgeon may change the cutting accessory 26 used with the surgical tool system 20. In order to make this change, the cone sleeve 146 is pushed rearwardly towards the handpiece base 90. This rearward motion is transmitted by the plunger 224 and the reach rod 216 to the trolley 206. The rearward movement of the trolley 206 displaces the magnet 204 relative to the handpiece state sensor 240. As a consequence of the displacement of the magnet 204, the output signal from the handpiece state sensor 240 changes state.

Once processor 36, in step 250, determines that the handpiece state sensor output signal has changed state, the processor proceeds to execute step 254. In step 254 the processor 36 causes an image to be displayed that instructs the surgeon that it is necessary to again calibrate the handpiece-sensing unit-cutting accessory sub-assembly to account for the position of the new cutting accessory relative to the sensing element 38. Thus, once it is determined that the coupling assembly 50 has been shifted from the run to the accessory load state, the processor 36 stops generating images that depict the position of the cutting accessory relative to the patient.

The processor 36 then waits for the surgeon to recalibrate the sensing element for the new cutting accessory 26, as represented by step 256. Once this recalibration is performed, the processor 36 can re-execute step 252 and again generate images indicating the position the cutting accessory 26 relative to the patient's fixed tissue. During this subsequent time period when step 252 is being executed, the processor calculates the position of the cutting accessory based on the new calibration data obtained in step 256.

The surgical tool system of this invention is constructed so that the motor 44 is physically separated from the handpiece 48. The handpiece 48 itself is assembled so that the majority of its components are non-metallic. The few metallic components contained within the handpiece are formed from material that has a relatively low magnetic permeability. Collectively, these features ensure that when the surgical tool 24 is actuated, the handpiece 48 does not serve as either or source or a sink for electromagnetic radiation. Thus, the actuation of the surgical tool 24 does not appreciable disturb the electromagnetic field produced by the transmitter 32. Since the electromagnet field produced by the transmitter 32 is not disturbed, the sensing unit 34 produces output signals that accurately indicate its position relative to the transmitter. Thus, the image generating system 28 accurately produces images indicating where the cutting accessory is located within the patient's body even when the tool 24 is actuated.

Since the sensing unit 34 is removable from the handpiece 48, the sensing unit does not have to be formed out of components designed to withstand the sterilization environment (130° C., near 100% humidity at 155 cm Hg) to which the handpiece 48 is subjected after surgery.

Moreover, the handpiece 48 of this invention does more than serve as a device for transferring power to the cutting accessory 26. Handpiece 48 supports a line for introducing irrigating fluid to the patient through the cutting accessory 26. Further, the handpiece 48 serves as a conduit through which a suction is selectively drawn from the surgical site through the cutting accessory 26.

The surgical tool system of this invention is further constructed so that, when the cutting accessory 26 is replaced, the image generating system 28 will not generate an image that potentially incorrectly identifies the position of the cutting accessory 26. Only after the image generating system 28 is recalibrated for the new cutting accessory 26 will the system 28 again cause a display to be produced that indicates the location of the cutting accessory. Thus, one can couple a single handpiece 48 to the sensing unit 34, use the handpiece to drive different cutting accessories, and not be concerned that the image generating system 28 will produce images that incorrectly identify the location of the cutting accessory.

Collectively, the above features make the surgical tool system 20 of this invention well suited for energizing a powered surgical tool while simultaneously providing a presenting images that indicate where, within a patient, the tool is located.

It should be recognized that the foregoing description has been limited to one particular version of this invention. It will be apparent that variations can be made to this invention with some or all of the advantages thereof. For example, not all handpieces of this system may be provided with means for providing an irrigating fluid to and/or means for applying a suction to the surgical site. Similarly, in other versions of the invention, the power producing unit may be different from the described drive shaft 102. For instance in some versions of the invention, the handpiece may include a pneumatic motor formed from non-magnetic components. In other versions of the invention, the handpiece may consist of some sort of light-emitting device, i.e., a laser. In these versions of the invention, the cutting accessories would be replaceable light-transmitting devices.

Alternatively, the handpiece may include a motor made of non-metallic material, for example a motor made from piezoelectric material. In still other versions of the invention, the handpiece may include an ultrasonic transducer. In these versions of the invention, the cutting accessories are members designed to transfer the ultrasonic energy generated by the transducer to a surgical site distal from the handpiece. It should be recognized that, in the foregoing versions of the invention, if the energy-producing member the is substantially non metallic, the member may be provided in the handpiece. This would eliminate the need to provide the separate drive unit.

Moreover, it should be recognized that the handpiece may have a different shape from the illustrated elongated, pencil-shaped handpiece. For example in some versions of the invention, the handpiece may have body that approximates that of a drill or driver. In other words, the handpiece may have a handgrip and section above the handgrip from which the cutting attachment extends.

Similarly, there is no requirement that in each version of the invention, that the sensing unit 34 be removable from the handpiece 48. In some versions of the invention, the handpiece, the components forming the sensing element 238 and/or handpiece state sensor 240 may be contained in the handpiece base. An advantage of this version of the invention is that the conductors through which the signals from these components flow may be integrally contained within the cable supplying power to the handpiece.

It should further be recognized that the described coupling assembly 50 is only one type of coupling assembly that can be integrated into the surgical tool 24 of this invention. In other versions of the invention, the handpiece 48 may have other types of coupling assemblies designed to releasably secure very different types of cutting accessories.

Figure 12:
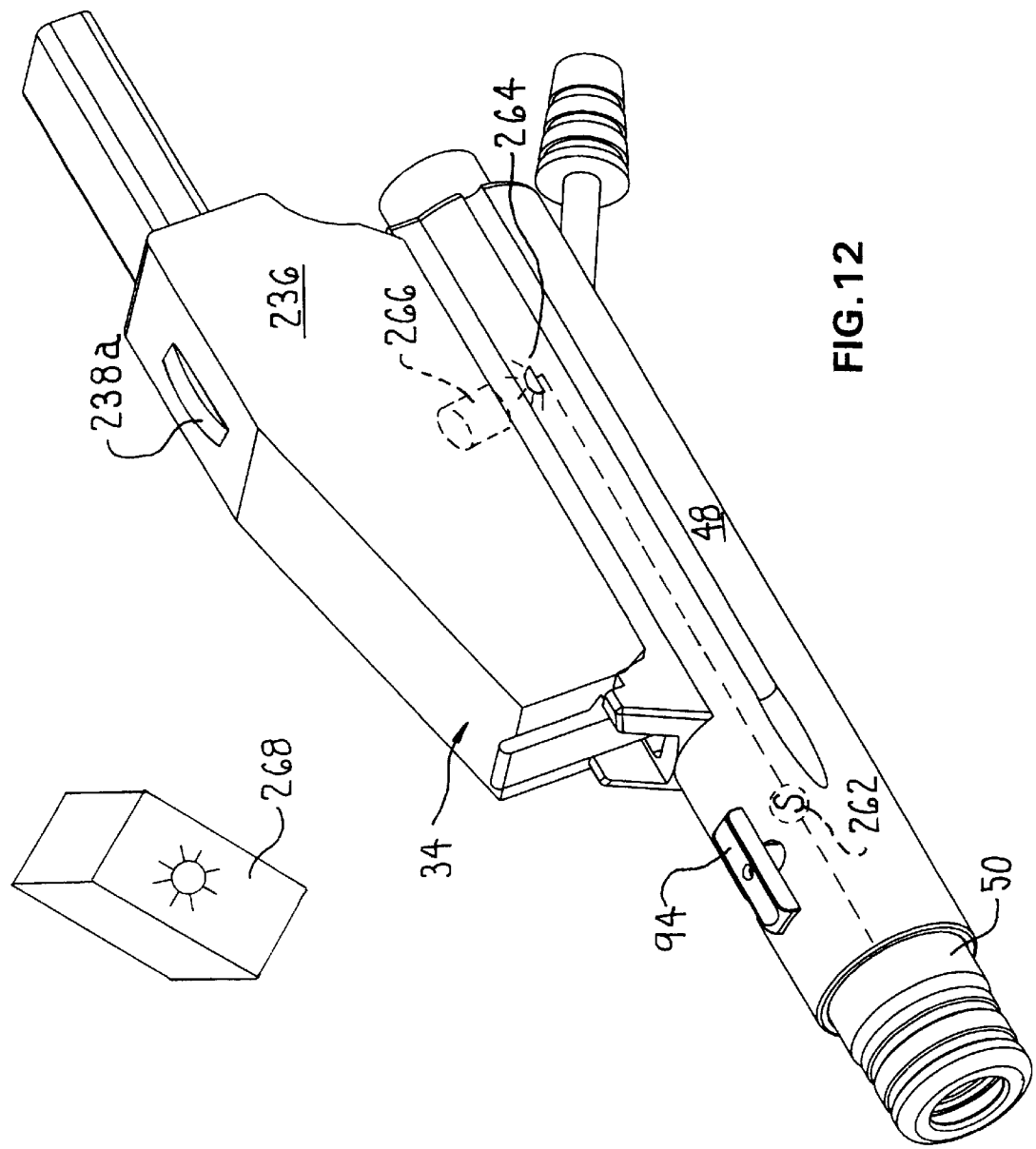
FIG. 12 depicts an alternative sensing unit and fixed unit of this invention.

Similarly, it should be understood that the state marker and complementary handpiece state sensor may be different from what has been described. For example in some versions of the invention, the state marker may be some type of light emitting or light reflecting element that travels on the trolley. In these versions of the invention, the handpiece state sensor may be some type of light sensitive transducer. Alternatively, the state marker may be some type of switch 202, as seen in FIG. 12 (as shown in phantom), connected to the coupling assembly 50 so that the open/closed state of the switch is a function of the run/accessory load state of the coupling assembly. For example, the switch could control the actuation of an LED 264 (as shown in phantom) that selectively directs light to an adjacent photovoltaic device 266 (as shown in phantom) that forms the handpiece state sensor. Alternatively, the voltage across the switch can be monitored by a device associated with processor 36. Changes in this voltage would then be recognized by the processor 36 as indicating the coupling assembly has transitioned between the run and accessory load states.

In still other versions of the invention, the state marker may undergo a state transition different from what has been described in response to the run/accessory load state transition of the coupling assembly 50. For example, the state marker could be a magnet or light transmitting/reflecting device that is directly mounted to the cone sleeve or other moving component of the coupling assembly 50. An advantage of this arrangement is that it reduces the overall number of components required to construct the handpiece.

It should likewise be understood that the surgical tool system 20 of this invention may be used with other image generating systems than the described system. For example, the system of this invention can be used with image generating systems in which a sensor 238a, as seen in FIG. 12, monitors light patterns generated by a static light transmitter 268 in order to provide output signals that indicate the position of the sensor. In still other versions of the invention, the sensor may include a set of accelerometers that provide an inertial data that is used to track the displacement of the handpiece and the position of the cutting accessories. Even with this type of image generating system, it is still necessary to initially calibrate the handpiece so the structure of the cutting accessory relative to the sensing unit is known.

Moreover, in some versions of the invention the sensing unit may not be the image generating system component integral with the handpiece. In some versions of the invention, the transmitter may be attached to the handpiece while the sensor remains at the fixed location. Accordingly, it should be clear that any type of sensing device integral with an image generating unit may be mounted to the handpiece 48.

Also, the processing steps executed by the image generating system 28 after a transition in the state of the coupling assembly 50 may significantly vary from what has been described. In some versions of the invention, once the state transition has been detected, processor 36 may only temporarily interrupt the display of the surgical site and cause the presentation of a warning message to the surgeon. Then, the surgeon could acknowledge receipt of the warning message, for example by depressing a touch-screen button. Once the button is depressed, the processor 36 would resume display of the body image and cutting accessory based on the old calibration data. This version of the system could be provided if the handpiece 48 was being used with a number of different cutting accessories that have the exact same shape. An advantage of this arrangement is that the surgeon would only have to calibrate the handpiece if it was be used with a cutting accessory that a different shape or dimensions than the previous cutting accessory.

Further, in some versions of the invention, the output signal from the handpiece state sensor 240 may be applied to the control console 45 that regulates the energization of the handpiece 48. In these versions of the invention, when the handpiece state sensor 240 indicates that the coupling assembly has undergone a run/accessory load state transition, the control console 45 may inhibit the further actuation of the handpiece until it has received an indication that the handpiece has been recalibrated for the new cutting accessory. In these versions of the invention, this indication may be in the form of a signal that is forwarded from the image generating system processor 36 to the control console 45. Alternatively, the control console 45 may be configured to simply require the surgeon to depress a button to affirm that the image generating system 28 has been recalibrated for the new cutting accessory 26.

Similarly, it should be recognized that the material from which the components of this surgical tool system are formed may be different from what has been described. For example, it may be possible to use non-metallic material other than the described plastics to form the plastic-formed components of the handpiece 48. Moreover, other low magnetic permeable material or even nonmagnetic material may be used to form the metal components of the handpiece.

Therefore, it is an object of the appended claims to cover all such variations and modifications that come within the true spirit and scope of this invention.

What is claimed is:

1. A surgical tool assembly comprising:
    a handpiece, said handpiece having:
        a base;
        a power producing assembly located in said base;
        a coupling assembly mounted to said base for releasably attaching an accessory to said handpiece so that the accessory receives power from said power producing assembly, said coupling assembly having a run state in which the accessory is attached to said coupling assembly and an accessory load state in which the accessory is removable from said coupling assembly; and
        a state marker attached to said coupling assembly, wherein the state of said state marker is controlled by said coupling assembly so that, when said coupling assembly undergoes a transition from the run state to the accessory load state, said state marker undergoes a state transition; and
    a sensing unit, said sensing unit comprising;
        a housing configured to be releasably secured to said base of said handpiece;
        a position-locating device disposed in said housing configured to produce signals used to determine the position of said sensing unit; and
        a handpiece state sensor fitted to said housing, said handpiece state sensor configured to monitor the state of said state marker and to produce a handpiece state signal representative of the state of said state marker.

2. The surgical tool assembly of claim 1, wherein: said power producing assembly is a rotating shaft; and said coupling assembly is configured to rotatably couple the accessory to said shaft.

3. The surgical tool system of claim 1, wherein:
    said state marker is mounted to said base to move within said base and is connected to said coupling assembly to move when said coupling assembly transitions from the run state to the accessory load state; and
    said handpiece state sensor is configured to monitor the position of said state marker and to generate the handpiece state sensor signal as a function of the relative position of said state marker to said handpiece state sensor.

4. The surgical tool system of claim 3, wherein said state marker is a magnet.

5. The surgical tool assembly of claim 1, wherein said position-locating device is configured to transmit signals to or receive signals from a fixed unit so that the position of said sensing unit can be determined.

6. The surgical tool system of claim 5, wherein said position-locating device is configured to receive signals broadcast by the fixed unit.

7. The surgical tool assembly of claim 5, wherein one of said position-locating device or the fixed unit transmits light and the other of the fixed unit or said position-locating device monitors the transmitted light so that the position of said sensing unit can be determined.

8. The surgical tool assembly of claim 7, wherein said position-locating device monitors light transmitted by the fixed unit and outputs signals representative of the position of said sensing unit.

9. The surgical tool assembly of claim 1, wherein:
    said state marker is a light-emitting device and said light-emitting device is connected to said coupling assembly so that the on/off state of said light-emitting device is set as a function of the run state/accessory load state of said coupling assembly; and
    said handpiece state sensor is configured to monitor the light emitted by said light-emitting device.

10. A method of performing image-guided surgery including the steps of:
    providing a handpiece with:
        a power generating unit;
        a coupling assembly for releasably connecting a cutting accessory to the power generating unit, the coupling assembly having a run state in which the cutting accessory is coupled to the power generating unit and an accessory load state in which the coupling accessory is removable from the power generating unit; and
a state marker that indicates when the coupling assembly transitions from the run state to the accessory load state;

removable mounting a sensing unit to the handpiece, the sensing unit having:
a sensing device for generating signals indicating the position of the device relative to a surgical site; and
a handpiece state sensor for monitoring the state marker;

calibrating the sensing for the cutting accessory coupled to the power generating unit;

actuating the power generating unit in the handpiece to cause the actuation of the cutting accessory;

generating an image indicating the position of the cutting accessory relative to the surgical site based on the signals generated by the sensing device and said calibration of the sensing unit;

selectively replacing the cutting accessory coupled to the handpiece while the sensing unit remains attached to the handpiece by displacing the coupling assembly from the run state to the accessory load state; and monitoring the state marker with the handpiece state sensor and, when the state marker indicated that the coupling assembly is transitioned from the rum state to the accessory load state, inhibiting the generation of subsequent images indicating the position of the cutting accessory until said step of calibrating the sensing unit is re-executed.

11. The method of claim 10, wherein the power generating unit is a rotating shaft, and the rotating shaft is actuated by energizing a drive motor that is separate from the handpiece and transferring the rotational power developed by the drive motor to the rotating shaft over a flexible drive shaft.

12. The method of claim 10, wherein:
the state marker is configured to move relative to the handpiece state sensor and is coupled to the coupling accessory to be physically displaced upon the transition of the coupling accessory from the run state to the accessory load state; and
the handpiece state sensor monitors the state marker by monitoring the physical displacement of the state marker.

13. The method of claim 10, wherein:
the state marker is a magnet that is physically displaced upon the transition of the coupling accessory from the run state to the accessory load state; and
the handpiece state sensor monitors the strength of a magnetic field of said magnet to determine the run/accessory load state of the coupling assembly.

14. The method of claim 10, wherein:
the sensing device of the sending unit transmits signals to or receives signals from a fixed unit; and
based on the signals received by the fixed unit or the sensing device, either the fixed unit of the sensing device generates signals used to determine the position of the sensing unit.

15. The method of claim 14, wherein one of the sensing device or the fixed unit transmits light signals and the other of the fixed unit or the sensing device monitors the emitted light and, based on the emitted light, generates the signals used to determine the position of the sensing unit.

16. The method of claim 10, wherein:
the state marker selectively generates a state marker signal as a function of the run state/accessory load state setting of the handpiece coupling assembly;
the handpiece state sensor monitors the state marker to determine whether or not the state marker is producing the state marker signal.

17. The method of claim 10, wherein the power generating unit is a rotating shaft, and the rotating shaft is actuated by energizing a drive motor.

18. The method of claim 10, wherein: the sensing device of the sensing unit receives signals broadcast by a fixed unit and, based on the signal receive from the fixed unit, the sensing device generated signals used to determine the position of the sensing unit.

19. The method of claim 10, wherein:
a fixed unit transmits light towards the sensing device of the sensing unit; and
the sensing device, based on the receipt of light transmitted from the fixed unit, generated signals representative of the position of the sensing unit.

* * * * *

UNITED STATES PATENT AND TRADEMARK OFFICE
CERTIFICATE OF CORRECTION

PATENT NO. : 6,332,891 B1
DATED : December 25, 2001
INVENTOR(S) : David M. Himes Page 1 of 1

It is certified that error appears in the above-identified patent and that said Letters Patent is hereby corrected as shown below:

Title page,
ABSTRACT,
Line 5, change "releasbly holds" to -- releasably holds --
Line 10, change "releasbly attached" to -- releasably attached --

Column 17,
Line 9, change "removable mounting" to -- removably mounting --
Line 29, change "marker indicated" to -- marker indicates --
Line 30, change "rum state" to -- run state --

Column 18,
Line 15, change "unit of the" to -- unit or the --
Line 36, change "device generated signals" to -- device generates signals --
Line 43, change "generated signals" to -- generates signals --

Signed and Sealed this

Twenty-eighth Day of May, 2002

Attest:

JAMES E. ROGAN
Attesting Officer                Director of the United States Patent and Trademark Office